(12) United States Patent
Hoermann

(10) Patent No.: US 12,239,295 B2
(45) Date of Patent: Mar. 4, 2025

(54) FLUID DISTRIBUTOR FOR A REPROCESSING DEVICE FOR REPROCESSING A SURGICAL INSTRUMENT

(71) Applicant: OLYMPUS Winter & Ibe GmbH, Hamburg (DE)

(72) Inventor: Mathis Jonathan Hoermann, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 375 days.

(21) Appl. No.: 17/705,507

(22) Filed: Mar. 28, 2022

(65) Prior Publication Data

US 2022/0313073 A1  Oct. 6, 2022

(30) Foreign Application Priority Data

Apr. 1, 2021 (DE) ...................... 10 2021 108 369.9
Mar. 1, 2022 (EP) ..................................... 22159359

(51) Int. Cl.
*A61B 1/12* (2006.01)
*B08B 9/032* (2006.01)

(52) U.S. Cl.
CPC .............. *A61B 1/125* (2013.01); *A61B 1/123* (2013.01); *B08B 9/0325* (2013.01); *B08B 2209/032* (2013.01)

(58) Field of Classification Search
None
See application file for complete search history.

(56) References Cited

U.S. PATENT DOCUMENTS

| | | | |
|---|---|---|---|
| 9,649,019 B2 | 5/2017 | Noack | |
| 2007/0102044 A1* | 5/2007 | Patzek, IV | ............. A61B 1/125 137/212 |
| 2014/0190520 A1* | 7/2014 | Noack | .................... A61B 1/125 134/113 |
| 2017/0367570 A1 | 12/2017 | Tobian | |
| 2020/0375434 A1* | 12/2020 | Scutti | ................ A61B 1/00137 |

FOREIGN PATENT DOCUMENTS

| | | |
|---|---|---|
| DE | 44 23 730 A1 | 1/1996 |
| DE | 10 2011 082 776 A1 | 3/2013 |
| DE | 10 2015 203 429 A1 | 9/2016 |
| EP | 2 594 220 A1 | 5/2013 |

* cited by examiner

*Primary Examiner* — Cristi J Tate-Sims
(74) *Attorney, Agent, or Firm* — Scully, Scott, Murphy & Presser, P.C.

(57) ABSTRACT

A fluid distributor for use with a reprocessing device for reprocessing a surgical instrument having a plurality of channels, including: a routing body having a plurality of connections corresponding to the channels; and a switching body movably disposed in the routing body, the switching body having an interior supply line connected to a fluid reservoir for selectively providing a fluid to one or more of the connections. The switching body can be configured such that, in a first position of the switching body relative to the routing body, the connections of the routing body are each in fluid communication with the supply line of the switching body and in at least a second position of the switching body relative to the fluid routing body less than all of the connections of the routing body are in fluid communication with the supply line of the switching body.

19 Claims, 3 Drawing Sheets

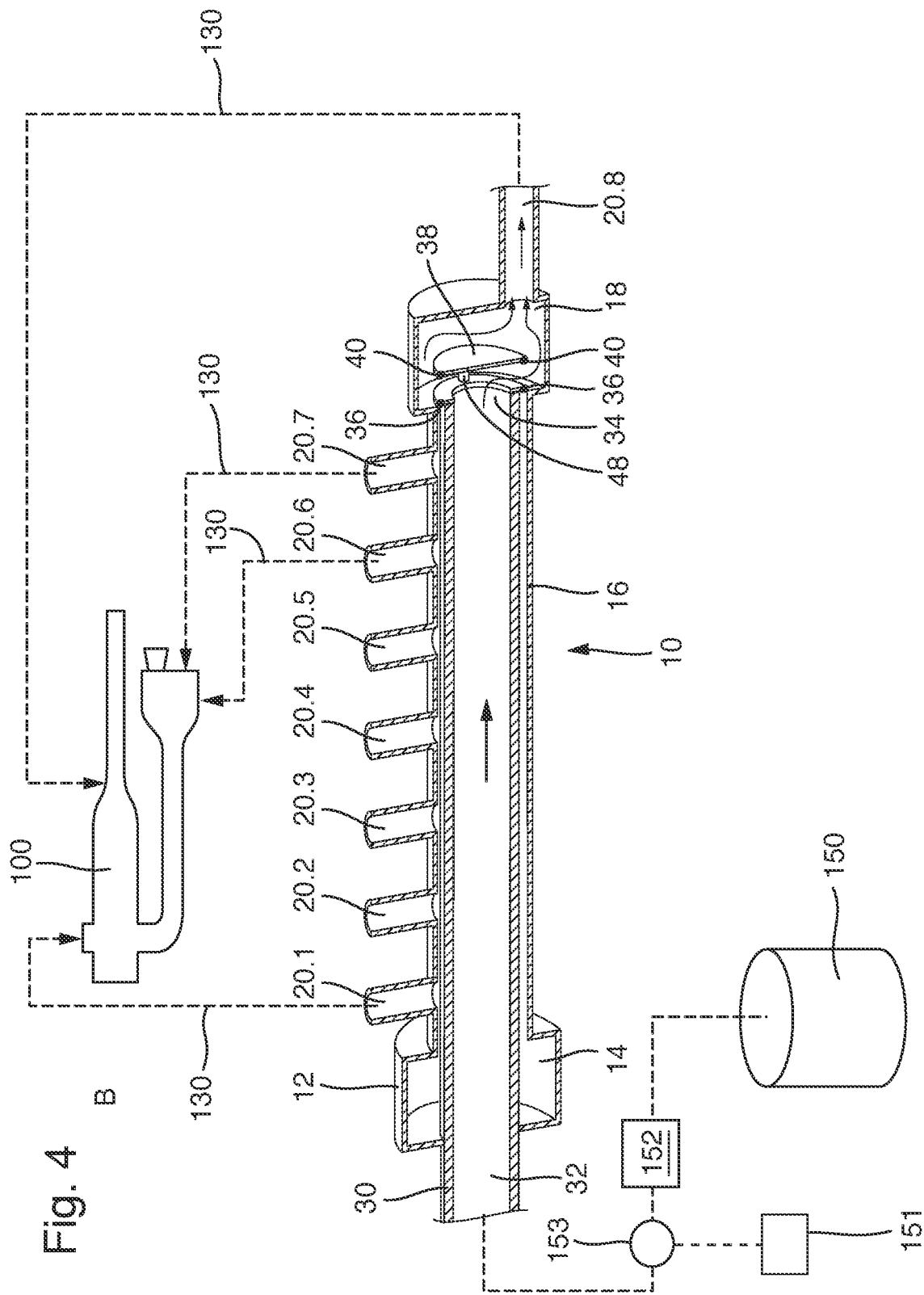

FLUID DISTRIBUTOR FOR A REPROCESSING DEVICE FOR REPROCESSING A SURGICAL INSTRUMENT

CROSS-REFERENCE TO RELATED APPLICATION

The present application is based upon and claims the benefit of priority from DE 10 2021 108 369.9 filed on Apr. 1, 2021, and EPO 22 159 359.3 filed on Mar. 1, 2022, the entire contents of each of which is incorporated herein by reference.

BACKGROUND

Field

The present disclosure relates to a fluid distributor for a reprocessing device for reprocessing a surgical instrument, such as an endoscope. Moreover, the present disclosure relates to a reprocessing device for reprocessing a surgical instrument, such as an endoscope, as well as a use of a fluid distributor in a reprocessing device.

Prior Art

It is known in the prior art that endoscopes are used to diagnose and treat diseases. For the use of endoscopes as well as other surgical appliances these surgical instruments must be reprocessed, i.e., cleaned and disinfected, after being used on a patient.

In the case of the reprocessing of surgical instruments, legal and clinical regulations must be strictly adhered to so that the components inside such as endoscope channels and on the surface of the surgical instruments, such as endoscopes, are disinfected and must be free of germs, bacteria, etc.

Reprocessing devices of surgical instruments, such as endoscopes, have devices which clean and disinfect the outer surfaces of the surgical instruments as well as the inner channels and channel systems using appropriate liquids. Rinsing cycles are normally provided for this. In the case of the inner channel rinsing of a surgical instrument, such as, of an endoscope or a flexible endoscope, the sanitary result of the reprocessing depends on the flow volume of a reprocessing fluid. Liquids or gases can serve as the reprocessing fluid.

Moreover, a reprocessing device from Olympus Winter & Ibe GmbH, Hamburg, under the name ETD is known for reprocessing and disinfecting flexible endoscopes. In this reprocessing device, the channels of the endoscopes are rinsed with a reprocessing fluid or respectively rinsing, cleaning and/or disinfecting liquids through mechanical cleaning and disinfection of, for example, endoscopes, such as flexible endoscopes.

Particular importance is ascribed to the cleaning and disinfection of the endoscope channels when reprocessing the surgical instruments, such as endoscopes. To reprocess the surgical instruments, the channels of the surgical instruments are connected to a rinsing circuit of the reprocessing device. To reprocess the endoscope channels, the channels are, for example, connected to an adapter of a receiving basket in which the endoscope to be cleaned is arranged so that subsequently, when introducing the receiving basket with the endoscope to be cleaned into the rinsing chamber of the reprocessing device, the channels are connected to rinsing channels of the rinsing circuit or the adapter is connected to a counterpart of the rinsing circuit.

The channels of the endoscope are coupled to a rinsing circuit provided in the rinsing chamber by plug-in couplings or screwed joints, wherein the channels are connected individually and sequentially to lines of the rinsing circuit. In addition, it is possible to connect the adapter and counterpart to each other.

Stop valves, Y-hose connecting pieces or directional valves which are bypassed and joined in a time-consuming manner and frequently involving much loss, exist for supplying fluids (i.e., liquids and gases) to channels to be cleaned and/or dried, or respectively in the rinsing circuit. In this context, the fluids flow through channels and can be distributed to a plurality of hoses.

Furthermore, a fluid distributor for a reprocessing device for reprocessing surgical instruments is known from DE 10 2015 203 429 A1. In addition, DE 10 2011 082 776 A1 discloses a device for rinsing channels of an endoscope.

SUMMARY

An object is to provide a simply structured fluid distributor and a reprocessing device for reprocessing a surgical instrument, such as an endoscope, wherein the fluid distributor can be usable in a flexible manner for the cleaning and/or drying of a plurality of channels, or respectively for the reprocessing of surgical instruments.

Such object can be achieved by a fluid distributor for a reprocessing device for reprocessing a surgical instrument, such as an endoscope, with a fluid routing body, such as an outer fluid routing body, wherein the fluid routing body has a plurality of individual connections, each for one channel to be cleaned and/or dried of a surgical instrument, wherein a movable fluid switching body can be provided in the fluid routing body, wherein the fluid switching body has in the interior a supply line, connectable or connected to a fluid reservoir, for supplying a fluid to the connections of the fluid routing body, wherein the movable fluid switching body is configured such that, in a first position of the fluid switching body in the fluid routing body, a plurality of or all connections of the fluid routing body can be fluidically connected to the supply line of the fluid switching body simultaneously, so that fluid can be supplied or is supplied to the plurality of or all connections of the fluid routing body simultaneously via the one supply line of the fluid switching body, and that in at least one further position of the fluid switching body in the fluid routing body, one of the plurality of connections of the fluid routing body can be fluidically connected to the supply line of the fluid switching body so that the fluid can be supplied to the one connection of the fluid routing body via the one supply line of the fluid switching body.

With such fluid distributor, a plurality of or all connections of the fluid routing body can be selectively fluidically connected to the supply line of the fluid switching body simultaneously or that only individual connections of the fluid routing body can be each fluidically connected to the supply line of the fluid switching body. The outer fluid routing body can be configured as a type of fluid distributing body with a plurality of connections for the channels of the surgical instrument to be cleaned and/or dried so that, depending on the placement or respectively position of the fluid switching body within the fluid routing body, the connections of the fluid routing body can be connected or respectively coupled fluidically to the supply line of the fluid switching body. Thus, with n (n=2, 3, 4, 5 . . . ) connections on the fluid routing body, the fluid switching body can be positioned or respectively is positionable inside the fluid routing body in (n+1) positions, in order to either fluidically connect all connections of the fluid routing body simultaneously to the supply line of the fluid switching body or to fluidically connect each of the connections of the fluid routing body to the supply line of the fluid switching body separately or respectively individually.

The fluid routing body and the fluid switching body can be moved or movable relative to each other for a position change of the fluid switching body within the fluid routing body.

In one position of the fluid switching body within the fluid routing body, the fluid is supplied from a fluid reservoir, for example, to a central hollow cylinder of the fluid routing body with only one opened connection of the fluid routing body, which is connected to a channel to be rinsed of a surgical instrument via a supply line or respectively rinsing line, wherein in one embodiment the supply of the fluid is monitored. The supply of the fluid can be controlled by the movable fluid switching body, which can be configured, for example, as a movable tube, so that fluid flows through either all connections simultaneously or only one outlet of the fluid routing body in each case.

By means of the fluid distributor, it is possible to variably rinse the channels of a surgical instrument, wherein the monitoring of the processes in the reprocessing device, or respectively the cleaning and disinfecting devices or respectively the drying and storage devices, for surgical instruments can be improved in a simple manner.

When cleaning and/or reprocessing surgical instruments, rinsing liquids and/or rinsing gases, depending on the process step to be performed, are supplied to the channels of the surgical instrument as a fluid for the respective processes by means of the fluid distributor. During the reprocessing of the surgical instruments, a leak-tightness test, in which a fluid, such as a liquid, can be supplied, for example, to the interior to the channels of an endoscope, can also be performed using the fluid distributor. In the process, the pressure, for example, of the fluid can be monitored during the reprocessing process, or respectively during the leak-tightness test, by means of a sensor, for example.

The fluid distributor can be used in a drying device, such as a drying cabinet, and/or in a storage device, such as a storage cabinet. In this case, for example, dry air or respectively compressed air can be conducted as the fluid on the input side via the fluid switching body of the fluid distributor to at least one of the connections of the fluid routing body into a connection, connected to the fluid routing body, to one of the channels or to the channels in a surgical instrument, such as an endoscope, in order to dry the channel or channels of the surgical instrument after a cleaning and disinfecting process, for example, in a cleaning and disinfecting device. Depending on the placement or respectively positioning of the fluid switching body in the fluid routing body, air or compressed air, such as dry air, can be applied to one connection or a plurality of, such as all, connections of the fluid routing body. In the case of a drying device, such as a drying cabinet, and/or storage device, such as a storage cabinet, for surgical instruments, a gaseous fluid, such as dry air or compressed air, can be used as the process fluid.

In addition, the fluid distributor can also be used for leak-tightness measurements, wherein for this purpose the pressure curve in the interior, or respectively the pressure curves in the individual channels, of a surgical instrument can be measured. In this case, a fluid, such as air, can be applied to individual channels of the surgical instrument using the fluid distributor, in order to detect or respectively determine the leak-tightness of the instrument depending on the measured pressure curves in the individual channels of the surgical instrument. In addition, a fluid, such as a gaseous fluid, such as air, can also be applied simultaneously to all individual channels in a corresponding position of the fluid switching body. This makes it possible to monitor the leak-tightness of the channels of the surgical instrument or the leak-tightness of the interior of the surgical instrument, respectively.

In addition, the fluid distributor can enable the blocking of individual channels of the surgical instrument, such as an endoscope, to be detected in a simple manner, for example, during the reprocessing and/or drying by means of corresponding process fluids.

It is also provided that the fluid distributor can be used to check and/or monitor the coupling of individual or all channels to be rinsed of the endoscope to an adapter for the endoscope channels. This can take place both during the cleaning and during the drying of the endoscope channels. As a result, it is possible, for example, to detect or find a loss of connectivity from the adapter to the endoscope in a simple manner.

The fluid switching body can be movable in the fluid routing body such that, in a first position of the fluid switching body in the fluid routing body, all connections of the fluid routing body can be fluidically connected simultaneously, such as in parallel, to the one supply line of the fluid switching body and, after the fluid switching body is moved from the first position into other, such as selectable, positions of the fluid switching body in the fluid routing body, one of the connections of the fluid routing body for each of the channels to be cleaned and/or dried of the surgical instrument can be fluidically connected individually to the one supply line of the fluid switching body.

In order to fluidically connect the connections of the fluid routing body to the supply line of the fluid switching body in a simple manner, the fluid switching body can be moved linearly within the fluid routing body. To clean or respectively to rinse the channels of the surgical instrument, such as an endoscope, that are connected to the connections of the routing body, for example, via corresponding rinsing lines, the fluid switching body can be connected, for example, to a reservoir for a process fluid so that the process fluid is conducted out of the reservoir for the process fluid through the supply line of the fluid switching body to the respectively opened connections of the fluid routing body.

For this purpose, the supply line of the fluid switching body can be configured as a tube, such as a hollow cylindrical tube, such as being a hollow cylindrical tube portion received in the fluid routing body. In this case, the supply line, or respectively the tube or the tube portion, can be at least partially received in the interior of the fluid routing body, depending on the placement or respectively position of the movable fluid switching body.

In order to conduct the liquid or gaseous fluid from a reservoir to the connections of the fluid routing body, the fluid routing body, the tube of the fluid switching body or the tube portion of the fluid switching body can be sealed off from the inside of the fluid routing body on the end side or front side using a seal, such as a sealing lip or an O-ring, wherein the seal can be configured as an annular collar. The annular collar can be configured as a seal on the front-face outlet of the fluid switching body.

In addition, the tube can have a front-face outlet in the fluid routing body or the tube portion can have a front-face outlet in the fluid routing body. The fluid can be conducted through the outlet of the tube or respectively the tube portion to the openings of the connections in the fluid routing body.

Inside the fluid routing body, a movable, such as linearly movable, sealing cover, such as being a disk-shaped sealing cover, that interacts with the outlet of the tube or with the outlet of the tube portion can be provided, wherein the sealing cover can be connected to the tube or to the tube portion and can be arranged at a predetermined distance from the outlet of the tube or from the outlet of the tube portion. By means of the sealing cover it is achieved that, within the fluid routing body, with a corresponding positioning of the fluid switching body, only one connection of the fluid routing body can be fluidically connected to the supply line of the fluid switching body. As a result, the fluid from the fluid reservoir flows through only one connection of the fluid routing body, wherein the tube or the tube portion of the fluid switching body can be sealed off, along with the sealing cover, from the interior of the fluid routing body.

The sealing cover can be connected to the tube or the tube portion at a predetermined distance, wherein the sealing cover can also be moved or can be moved simultaneously with the movement of the fluid switching body. The sealing cover can be connected to the fluid switching body via at least one spacer. The sealing cover can be arranged here at a predetermined, constant distance from the front face, having the outlet, of the fluid switching body.

The sealing cover can be sealed off from the inside of the fluid routing body using a seal, such as a sealing lip or an O-ring, on the circumferential edge of the sealing cover.

The fluid routing body can have an elongated, such as cylindrical or hollow cylindrical, tube body with an interior for receiving the fluid switching body and at least one flow chamber connected to the tube body for receiving an end of the fluid switching body, wherein the tube body can be arranged between two flow chambers. When the fluid switching body is arranged in the flow chamber, all connections of the routing body can be fluidically connected to the supply line.

The tube body can have a plurality of connections arranged next to each other, each for one channel of the surgical instrument, such as at equidistant distances, and/or that the at least one flow chamber can have a connection for a channel of the surgical instrument. If, for example, two flow chambers are arranged one on each end of the tube body, in relation to the flow direction of the fluid, the first flow chamber can only be fluidically with the tube body and a flow chamber downstream, or respectively on the output side, after the tube body has a connection for a channel of the surgical instrument.

The interior of the tube body of the fluid routing body can have a cross-section and the flow chamber can have an interior with a cross-section, wherein the cross-section of the interior of the tube body can be smaller than the cross-section of the interior of the flow chamber, which can be aligned parallel to it.

A drive for the fluid switching body can be provided to move the fluid switching body, wherein the drive can be configured as a mechanical drive, as an electric drive, as a pneumatic drive, as a magnetic drive or as a hydraulic drive. A position sensor device can be provided for detecting at least one position or a plurality of positions of the fluid switching body within the fluid routing body, wherein the position sensor device can be configured as an optical sensor or as a mechanically working sensor or as an electrical sensor.

Furthermore, such object can be achieved by a reprocessing device for reprocessing a surgical instrument, such as an endoscope, with a fluid distributor, described above. To avoid repetitions, reference is expressly made to the above embodiments.

In addition, such object can be achieved by the use of a fluid distributor, as described above, in a reprocessing device for reprocessing a surgical instrument, in addition an endoscope. Reference is made accordingly to the embodiments above.

In one embodiment, the reprocessing device can be configured as a cleaning and/or disinfecting device or as a drying and/or storage device for surgical instruments, such as endoscopes.

BRIEF DESCRIPTION OF THE DRAWINGS

Further features will become evident from the description of embodiments, together with the claims and the appended drawings. Embodiments can fulfill individual features or a combination of several features.

The embodiments are described below, without restricting the general idea of the invention, based on exemplary embodiments in reference to the drawings, whereby we expressly refer to the drawings with regard to the disclosure of all details that are not explained in greater detail in the text. In the drawings:

FIG. 4 illustrates a schematic representation of a fluid distributor of a drying and storage device for a surgical instrument.

In the drawings, the same or similar elements and/or parts are, in each case, provided with the same reference numerals such that they are not introduced again in each case.

DETAILED DESCRIPTION

Figure 1:
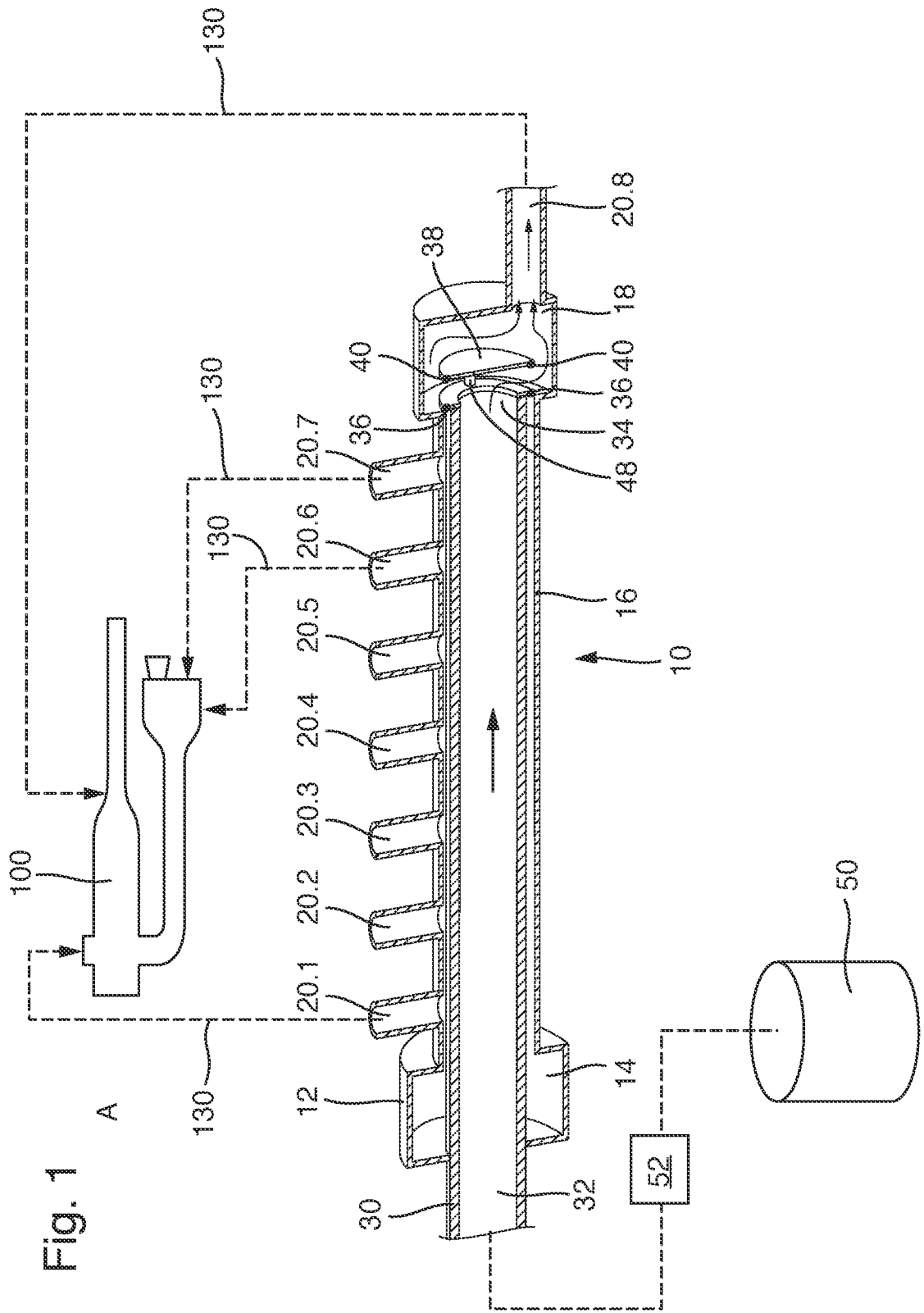
FIG. 1 illustrates a schematic representation of a fluid distributor of a reprocessing device for a surgical instrument.

FIG. 1 shows a fluid distributor 10 for corresponding fluids, such as liquids or gases. The fluid distributor 10 is a component of a schematically illustrated reprocessing device A for an endoscope 100. The endoscope 100 here has channels which are to be cleaned and disinfected.

For this purpose, a rinsing fluid is conveyed to the fluid distributor 10 from a rinsing agent reservoir 50 by a pump 52. The fluid distributor 10 has an outer fluid distributing body 12, which on the input side has a first flow chamber 14 that is connected to a tube cylinder 16. On the output side, the tube cylinder 16 is connected to a flow chamber 18. The flow chamber 18 also has a connection 20.8, which is connected to a rinsing line 130 for the endoscope 100.

The tube cylinder 16 also has connections 20.1 to 20.7 along its longitudinal extension, which are connected to corresponding rinsing lines 130. By way of example for illustration, only four rinsing lines 130 are drawn in FIG. 1. The rinsing lines 130 themselves are provided with corresponding connections to the endoscope 100 in order to clean or respectively to disinfect the corresponding channels (not shown here) in the endoscope 100.

Inside the fluid distributor 10, a fluid switching body 30 is arranged which is linearly movable within the fluid routing body 12. The fluid switching body 30 is configured as a hollow cylindrical tube so that, inside the fluid switching body 30, a supply line 32 is configured, which is connected on the input side to the rinsing agent reservoir 50 via the pump 52. The fluid switching body 30 is also sealed on the input side of the (first) flow chamber 14.

A front-face outlet 34 is configured on the output side of the supply line 32 so that the rinsing fluid taken from the rinsing agent reservoir 50 is discharged out of the outlet 34. A collar-shaped seal 36 is arranged on the outside in the region of the front-face outlet 34 so that the outlet 34 of the supply line 32 is configured opposite the interior of the fluid routing body 12 in the region of the tube cylinder 16.

Furthermore, on the output side of the outlet 34 at a predetermined distance, a sealing cover 38 is arranged which is also configured with a circumferential seal 40 on its outer side. The sealing cover 38 is firmly connected to the front face of the supply line 32 by means of a spacer 48.

In FIG. 1, the fluid switching body 30 is arranged in an (end) position in the fluid routing body 12 so that the outlet 34 faces the (second) flow chamber 18 and the rinsing fluid conveyed through the supply line 32 is introduced into the flow chamber 18. The flow chamber 18 here is larger in cross-section than the cross-sectional surface of the sealing cover 38. As a result, the rinsing medium flows through the supply line 32 via the outlet 34 into the flow chamber 18, wherein the rinsing medium is supplied on the end side only via the outlet 20.8 of the rinsing line 130 connected thereto, whereby the correspondingly connected channel of the endoscope 100 is rinsed when the fluid switching body 30 is in the position shown in FIG. 1. The rinsing fluid is not applied to the other outlets 20.1 to 20.7 according to the position of the fluid switching body 30 shown in FIG. 1.

Figure 2:
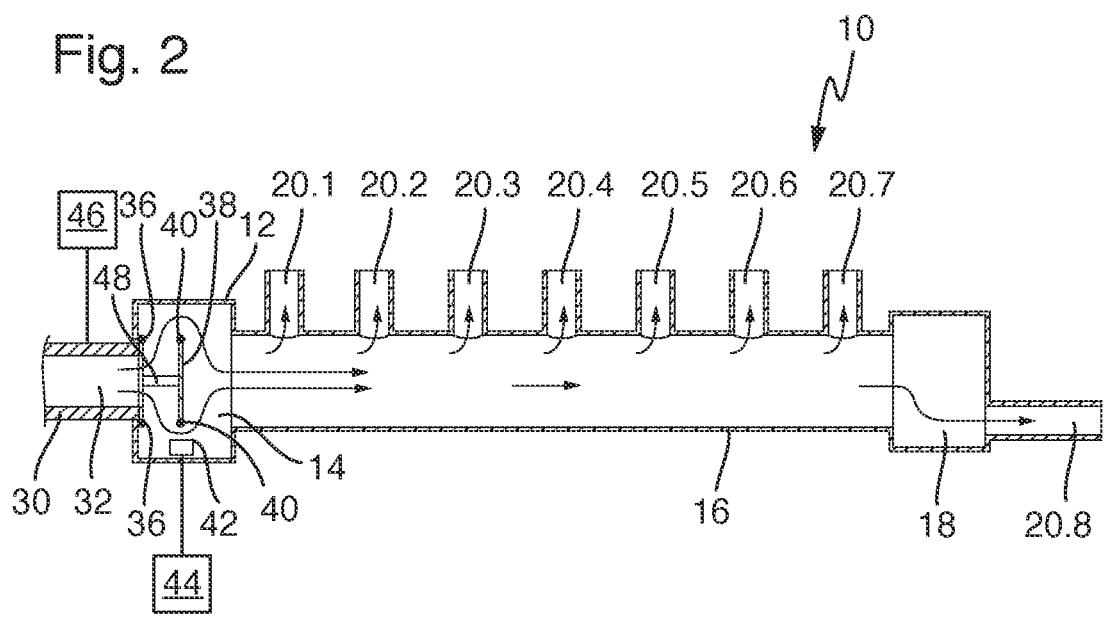
FIG. 2 schematically illustrates a cross-section through the fluid distributor and FIG. 3 schematically illustrates another representation of the fluid distributor in cross-section.
Figure 3:
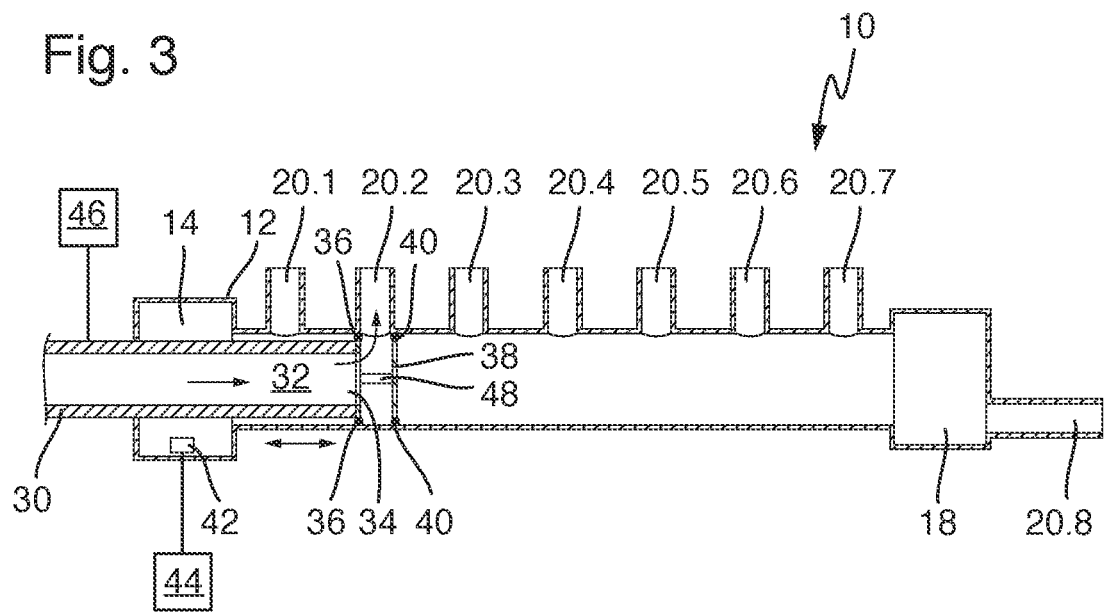

Additional representations of the fluid distributor 10 are shown in FIGS. 2 and 3, wherein the linearly movable fluid switching body 30 is shown in various positions here.

In the (starting) position of the fluid switching body 30 shown in FIG. 2, the outlet 34 of the supply line 32 is arranged within the first flow chamber 14 so that, when a rinsing fluid is conveyed, the rinsing fluid flows through all outlets 20.1 to 20.8 of the fluid routing body 12 simultaneously so that all channels of the endoscope 100 are rinsed simultaneously.

If the fluid switching body 30 is then moved linearly in the direction of the second flow chamber 18 by means of a drive 46, the rinsing medium flows successively in corresponding (intermediate) positions only through the individual outlets 20.1 to 20.8 separately in each case. Depending on the placement of the fluid switching body 30 within the fluid routing body 12, the connections 20.1 to 20.8 are activated individually here so that the rinsing fluid is always conducted only to one of the connections 20.1 to 20.8 to be rinsed and the channels lying behind or respectively connected thereto of the endoscope 100 via the individual open connections 20.1 to 20.8.

In FIG. 3, the fluid switching body 30 is positioned so that the rinsing medium flows through the outlet 20.2 only, while the rinsing medium does not flow through the other outlets 20.1, 20.3 to 20.8.

To detect the position of the fluid switching body 30, a measuring sensor 42, for example, is arranged in the first flow chamber 14, by means of which the corresponding positioning of the fluid switching body 30 within the fluid routing body 12 is detected. The corresponding measurement data from the measuring sensor 42 is forwarded in this case to a corresponding controller 44 of the reprocessing device.

The drive 46 for the fluid switching body 30 can be configured as an electric, hydraulic, pneumatic, magnetic or mechanical drive, and can have an actuator, such as a motor, in order to move the fluid switching body 30 back and forth linearly within the fluid routing body 12 along the longitudinal extension of the fluid routing body 12.

In FIG. 4, a fluid distributor 10 of a drying and storage device B for the endoscope 100 is shown schematically as another exemplary embodiment. In the drying and storage device B in FIG. 4, the fluid distributor 10 is configured accordingly as shown in FIG. 1, such that the previous explanations for the fluid distributor 10 in FIGS. 1 to 3 apply analogously.

To dry the individual channels 20.1 to 20.8 of the fluid routing body 12 and the channels of the endoscope 100 depending on the position of the fluid switching body with a process fluid, such as air or compressed air, a process fluid reservoir 150 is provided, which is connected to the fluid switching body 30 or respectively its supply line 32. A valve 152 and a sensor 153 are arranged in the connector between the process fluid reservoir 150 and the supply line 32.

The process fluid is conducted out of the process fluid reservoir 150 to the outlet 20.8 through the opening of the valve 152. The pressure of the process fluid in the line is measured by means of the sensor 153. The sensor 153 is furthermore connected to a leak-tightness tester 151 to test the leak-tightness of the channel, which is connected to the outlet 20.8, of the endoscope 100. The leak-tightness tester 151 can be a component of a control unit of the drying and storage device B.

When the fluid switching body 30 is positioned in the flow chamber 14 (cf. FIG. 2), the process fluid is applied to all channels of the endoscope 100 connected to the outlets 20.1 to 20.8. Depending on the positioning of the fluid switching body 30 in the tube body 16 (cf. FIG. 3), the process fluid is supplied to the individual channels of the endoscope 100 via the corresponding outlets 20.1 to 20.8.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

10 Fluid distributor
12 Fluid routing body
14 Flow chamber
16 Tube body
18 Flow chamber
20.1, . . . , 20.8 Outlets
30 Fluid switching body
32 Supply line
34 Outlet
36 Seal
38 Sealing cover
40 Seal
42 Sensor
44 Controller
46 Drive
50 Rinsing agent reservoir
52 Pump
100 Endoscope
130 Rinsing line
150 Process fluid reservoir
151 Leak-tightness tester 152 Valve
153 Sensor
A Reprocessing device
B Drying and storage device

What is claimed is:

1. A fluid distributor for use with a reprocessing device for reprocessing a surgical instrument having a plurality of channels, the fluid distributor comprising:
an exterior fluid routing body having an interior and a plurality of connections in fluid communication with the interior, the plurality of connections corresponding to the plurality of channels of the surgical instrument; and
an interior fluid switching body linearly movable within the interior of the exterior fluid routing body;
wherein the interior fluid switching body is a cylindrical tube having an interior supply line configured to be connected to a fluid reservoir for selectively providing a fluid from the fluid reservoir to one or more of the plurality of connections via the interior supply line.

2. The fluid distributor according to claim 1, wherein the interior fluid switching body is configured such that, in a first position of the interior fluid switching body relative to the exterior fluid routing body, the plurality of connections of the exterior fluid routing body are each in fluid communication with the interior supply line of the interior fluid switching body and in at least a second position of the interior fluid switching body relative to the exterior fluid routing body less than all of the plurality of connections of the exterior fluid routing body are in fluid communication with the interior supply line of the interior fluid switching body.

3. The fluid distributor according to claim 1, wherein the exterior fluid routing body is positioned radially outside the interior fluid switching body.

4. The fluid distributor according to claim 2, wherein the interior fluid switching body is movable in the exterior fluid routing body such that, in the first position all of the plurality of connections of the exterior fluid routing body are in fluid communication of the interior supply line of the interior fluid switching body and, in the second position, only one of the plurality of connections of the exterior fluid routing body is individually connected to the interior supply line of the interior fluid switching body.

5. The fluid distributor according to claim 1, wherein, in the exterior fluid routing body, the tube of the interior fluid switching body is sealed off from the inside of the exterior fluid routing body on one of an end face or a front face with a seal.

6. The fluid distributor according to claim 5, wherein the seal is an annular seal.

7. The fluid distributor according to claim 1, wherein the cylindrical tube of the interior fluid switching body has a front-face outlet.

8. The fluid distributor according to claim 7, further comprising a sealing cover disposed inside the exterior fluid routing body that interacts with the front-face outlet of the cylindrical tube.

9. The fluid distributor according to claim 8, wherein the sealing cover is configured to be movable with the interior fluid switching body.

10. The fluid distributor according to claim 8, wherein the sealing cover is connected to the cylindrical tube and is arranged at a predetermined distance from the outlet of the cylindrical tube.

11. The fluid distributor according to claim 8, wherein the sealing cover further comprises a seal for sealing off from the inside of the exterior fluid routing body.

12. The fluid distributor according to claim 11, wherein the seal is provided on a circumferential edge of the sealing cover.

13. The fluid distributor according to claim 1, wherein the exterior fluid routing body has an elongated tube body with the interior for receiving the interior fluid switching body and at least one flow chamber connected to the tube body for receiving an end of the interior fluid switching body.

14. The fluid distributor according to claim 13, wherein the tube body is cylindrical and is arranged between first and second flow chambers.

15. The fluid distributor according to claim 13, wherein at least a portion of the plurality of connections are arranged next to each other along a longitudinal direction of the tube body.

16. The fluid distributor according to claim 13, wherein the interior of the tube body of the exterior fluid routing body has a first cross-section and the first and second flow chambers have an interior with a second cross-section, wherein the first cross-section of the interior of the tube body is smaller than the second cross-section of the interior of the first and second flow chambers.

17. The fluid distributor according to claim 1, further comprising a drive for moving the interior fluid switching body, wherein the drive being one of a mechanical drive, an electric drive, a pneumatic drive, a magnetic drive or a hydraulic drive.

18. The fluid distributor according to claim 1, further comprising a position sensor device for detecting at least one position or a plurality of positions of the interior fluid switching body relative to the exterior fluid routing body, wherein the position sensor device is one of as an optical sensor, a mechanical sensor or an electrical sensor.

19. A reprocessing device comprising the fluid distributor according to claim 1.

* * * * *